United States Patent [19]
Ekins

[11] Patent Number: 5,834,319
[45] Date of Patent: Nov. 10, 1998

[54] BACK-TITRATION ASSAY USING TWO DIFFERENT MARKERS

[76] Inventor: Roger P. Ekins, Pondweed Place, Friday Street, Abinger, Common Dorking, Surrey, Great Britain, RH5 GJR

[21] Appl. No.: 663,172

[22] PCT Filed: Dec. 23, 1994

[86] PCT No.: PCT/GB94/02813

§ 371 Date: Jun. 14, 1996

§ 102(e) Date: Jun. 14, 1996

[87] PCT Pub. No.: WO95/18376

PCT Pub. Date: Jul. 6, 1995

[30] Foreign Application Priority Data

Dec. 24, 1993 [GB] United Kingdom .................. 9326451

[51] Int. Cl.⁶ ..................... G01N 33/543; G01N 33/566; G01N 33/53
[52] U.S. Cl. .................. 436/518; 436/501; 436/517; 436/63; 436/164; 436/800; 436/808; 435/7.1; 435/7.92; 435/973
[58] Field of Search ..................................... 436/518, 501, 436/517, 63, 164, 800, 808; 435/7.1, 7.92, 973

[56] References Cited

U.S. PATENT DOCUMENTS 5,171,695 12/1992 Ekins ...................................... 436/518
5,432,099 7/1995 Ekins ...................................... 436/518

FOREIGN PATENT DOCUMENTS

| 0304202 | 2/1989 | European Pat. Off. . |
| WO 8401031 | 3/1984 | WIPO . |
| WO 8801058 | 2/1988 | WIPO . |
| WO 8809503 | 12/1988 | WIPO . |

OTHER PUBLICATIONS

Berson and Yalow, "Methods in Investigative and Diagnostic Endocrinology", pp. 111–116 (1973).

*Primary Examiner*—Ponnathapura Achutamurthy
*Assistant Examiner*—P. Ponnaluri
*Attorney, Agent, or Firm*—Dann, Dorfman, Herrell and Skillman

[57] ABSTRACT

A method for determining the concentration of an analyte 6 in a liquid sample is described. The method uses a binding agent 2 capable of binding the analyte 6 and first and second developing agents 8, 12, the first developing agent 8 capable of binding to unoccupied binding sites on the binding agent 2 and having a first marker 10, the second developing agent 12 capable of binding to the bound analyte or to the occupied binding sites and having a second marker 14 different from the first. The concentration of the analyte is determined by measuring the signals from the markers on first and second developing agents 8, 12. Thus, the method combines the competitive and non-competitive methods of the prior art and preferably has the advantage of extending the working range and/or sensitivity of the assay. A kit for performing the assay is also disclosed.

31 Claims, 4 Drawing Sheets

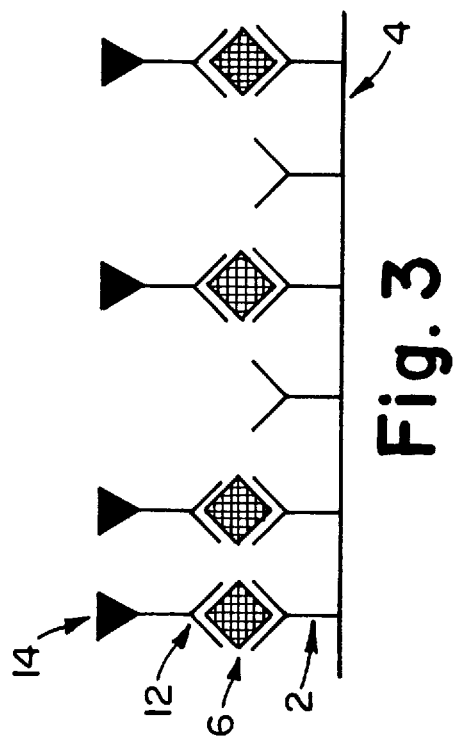
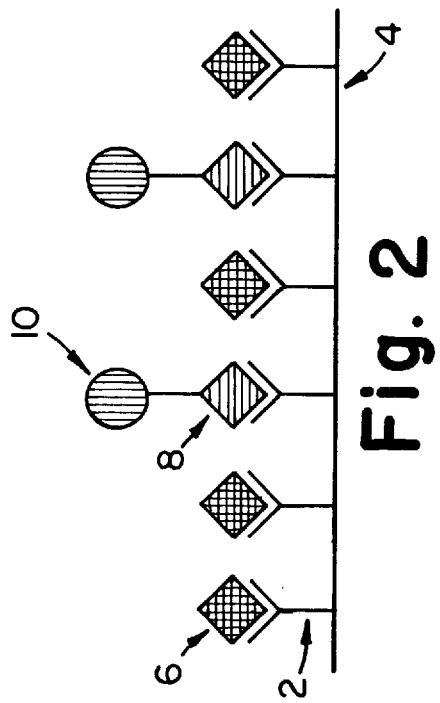
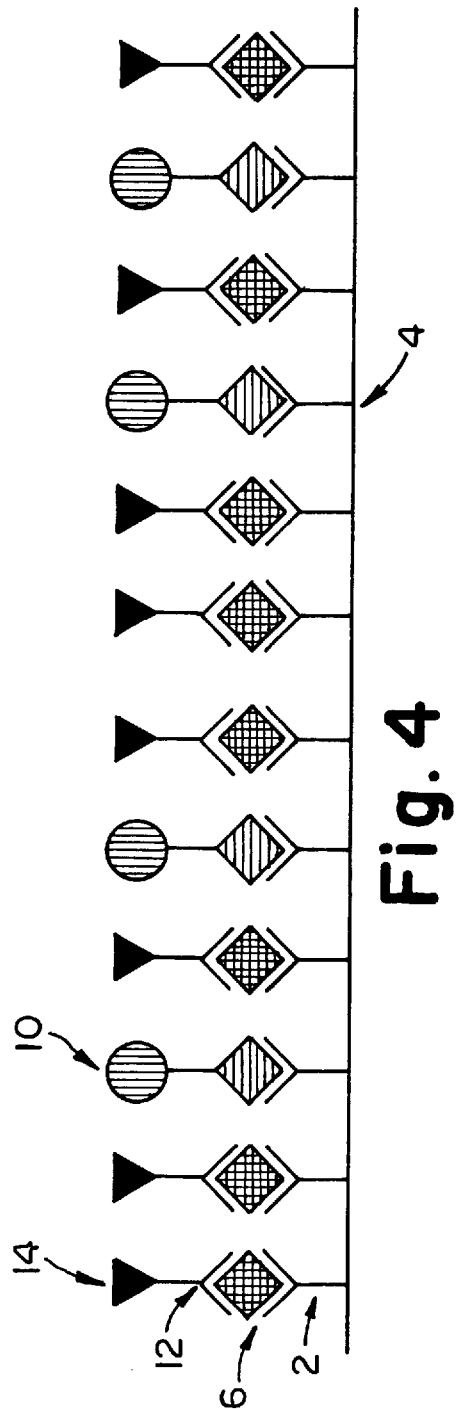

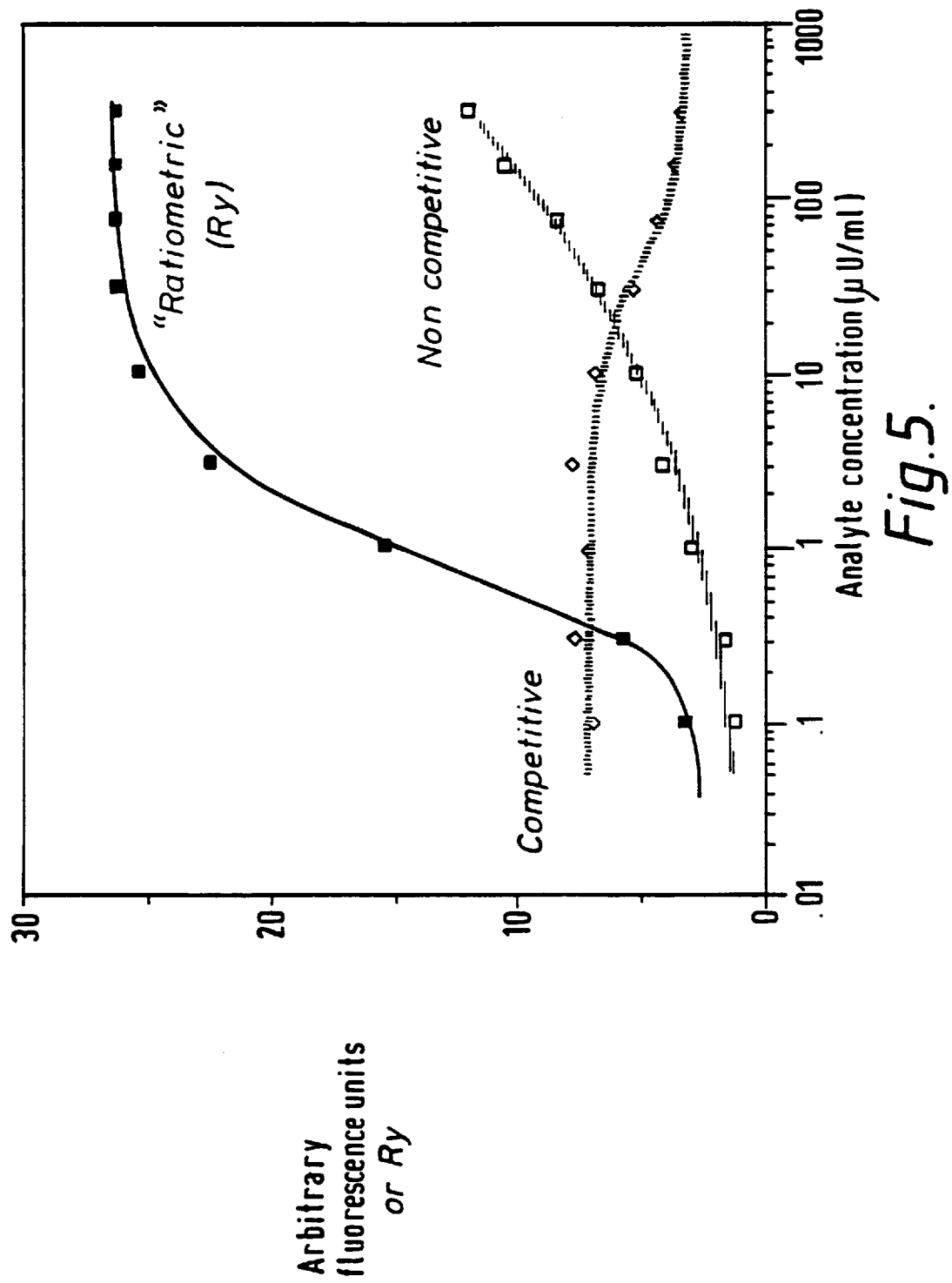

BACK-TITRATION ASSAY USING TWO DIFFERENT MARKERS

FIELD OF THE INVENTION

The present invention relates to binding assays, eg for determining the concentration of analytes in liquid samples.

BACKGROUND OF THE INVENTION

It is known to measure the concentration of an analyte, such as a drug or hormone, in a liquid sample by contacting the liquid with a binding agent having binding sites specific for the analyte, separating the binding agent having analyte bound to it and measuring a value representative of the proportion of the binding sites of the binding agent that are occupied by analyte (referred to as the fractional occupancy). Typically, the concentration of the analyte in the liquid sample can then be determined by comparing the fractional occupancy against values obtained from a series of standard solutions containing known concentrations of analyte.

In the past, the measurement of fractional occupancy has usually been carried out by back-titration with a labelled developing reagent using either so-called competitive or non-competitive methods.

In the competitive method, the binding agent having analyte bound to it is back-titrated, either simultaneously or sequentially, with a labelled developing agent, which is typically a labelled version of the analyte. The developing agent can be said to compete for the binding sites on the binding agent with the analyte whose concentration is being measured. The fraction of the binding sites which become occupied with the labelled analyte can then be related to the concentration of the analyte as described above.

In the non-competitive method, the binding agent having analyte bound to it is back-titrated with a labelled developing agent capable of binding to either the bound analyte or the occupied binding sites on the binding agent. The fractional occupancy of the binding sites can then be measured by detecting the presence of the labelled developing agent and, just as with competitive assays, related to the concentration of the analyte in the liquid sample as described above.

In both competitive and non-competitive methods, the developing agent is labelled with a marker to allow the developing agent to be detected. A variety of markers have been used in the past, for example radioactive isotopes, enzymes, chemiluminescent markers and fluorescent markers.

In the field of immunoassay, competitive assays have in general been carried out in accordance with design principles enunciated by Berson and Yalow, for instance in "Methods in Investigative and Diagnostic Endocrinology" (1973), pages 111 to 116. Berson and Yalow proposed that in the performance of competitive immunoassays, maximum sensitivity is achieved if an amount of binding agent is used to bind approximately 30 to 50% of a low concentration of the analyte to be detected. In non-competitive immunoassays, maximum sensitivity is generally thought to be achieved by using sufficient binding agent to bind close to 100% of the analyte in the liquid sample. However, in both cases immunoassays designed in accordance with these widely-accepted precepts require the volume of the sample to be known and the amount of binding agent used to be accurately known or known to be constant.

In International Patent Application WO84/01031, I disclosed that the concentration of an analyte in a liquid sample can be measured by contacting the liquid sample with a small amount of binding agent having binding sites specific for the analyte. In this method, provided the amount of binding agent is small enough to have only an insignificant effect on the concentration of the analyte in the liquid sample, it is found that the fractional occupancy of the binding sites on the binding agent by the analyte is effectively independent of the volume of the sample.

This approach is further refined in EP304,202 which discloses that the sensitivity and ease of development of the assays in WO84/01031 are improved by using an amount of binding agent less than 0.1 V/K moles located on a small area (or "microspot") of a solid support, where V is the volume of the sample and K is the equilibrium constant of the binding agent for the analyte.

In both these references, the fractional occupancy of the binding agent by the analyte is measured using either a competitive or a non-competitive technique, as described above.

There is a continuing need to develop binding assays having greater sensitivity, but that can also accurately measure analyte concentrations across a wider working range.

SUMMARY OF THE INVENTION

The present invention provides a method for determining the concentration of an analyte in a liquid sample comprising:

(a) contacting the liquid sample with a binding agent having binding sites specific for the analyte so that a fraction of the binding sites become occupied by the analyte;

(b) back-titrating the binding agent with first and second developing agents, the first developing agent capable of binding to unoccupied binding sites and having a first marker, the second developing agent capable of binding to the bound analyte or to the occupied binding sites and having a second marker different from the first;

(c) measuring the signals produced by the first and second markers to provide a value representative of the fraction of the binding sites occupied by the analyte; and, (d) comparing the value to corresponding values obtained from a series of standard solutions containing known concentrations of analyte to obtain the concentration of the analyte in the liquid sample.

Accordingly, the present invention provides a method of determining the concentration of an analyte which combines the competitive and non-competitive methods of the prior art. Preferably, this has the advantage of extending the working range over which an assay can provide results of a desired precision. This is explained further below.

Conveniently, the first and second markers are radioactive isotopes, enzymes, chemiluminescent markers or fluorescent markers. The use of fluorescent dye markers is especially preferred as the fluorescent dyes can be selected to provide fluorescence of an appropriate colour range (excitation and emission wavelength) for detection. Fluorescent dyes include coumarin, fluorescein, rhodamine and Texas Red. Fluorescent dye molecules having prolonged fluorescent periods can be used, thereby allowing time-resolved fluorescence to be used to measure the strength of the fluorescent signal after background fluorescence has decayed. Latex microspheres containing fluorescent or other markers, or bearing them on their surface can also be employed in this context. The signals from the markers can be measured using a laser scanning confocal microscope.

Typically, the binding agent is an antibody having binding sites for an antigen. Alternatively, the binding agent maybe an oligonucleotide capable of binding to a target nucleic acid molecule, eg by having a complementary sequence to the target nucleic acid molecule.

Preferably, a small amount of binding agent is used in accordance with the "ambient analyte" techniques of WO84/01031, so that the volume of the liquid sample need not be known. As discussed above, the amount of binding agent should be sufficiently small so that it does not significantly disturb the ambient concentration of analyte in the liquid sample. The use of an amount of binding agent which binds less than 5% of the analyte is preferred. However, the use of a smaller amount of binding agent, e.g. to bind 2% or 1% of the analyte, further reduces the disturbance to the ambient concentration of the analyte and helps to minimise the error in determining the analyte concentration.

More conveniently, the use of a concentration of binding agent not greater than 0.1 V/K, where V is the volume of the sample applied to the test zone and K is the association constant for analyte binding to the binding agent (as described in EP304,202), ensures that this condition is fulfilled regardless of the analyte concentration.

In one embodiment of the present invention, the concentration of a plurality of different analytes can be simultaneously determined using a plurality of different binding agents each having binding sites specific for a given analyte. In this case, preferably the binding agent is immobilised on a support at a discrete location, eg as a microspot.

In this embodiment, the same first and second developing agents can be used to back-titrate the plurality of different binding agents, the discrete locations containing the different binding agents being distinguished apart by their location on the support. Thus, it is possible to use a universal pair of developing agents, with the advantage that only two species of marker need to be detected.

Further, the binding agent having binding sites specific for a particular analyte can be immobilised on a support at a plurality of locations so that a series of replicate measurements of the concentration of that analyte can be made simultaneously.

Preferably, particularly when rapid measurements are required, and/or when sample volumes are in the order of 1 ml or less, the locations are microspots having an area of 1 mm$^2$. Furthermore, the binding agent should preferably be present at a high surface density within the microspot, thereby maximising sensitivity.

The present invention also includes a kit for determining the concentration of an analyte in a liquid sample according to the above method, the kit comprising:
(a) a solid substrate having attached thereto binding agent, the binding agent having binding sites specific for the analyte,
(b) back-titration reagents comprising first and second developing agents, the first developing agent capable of binding to unoccupied binding sites and having a first marker, the second developing agent capable of binding to the bound analyte or to occupied binding sites and having a second marker different from the first.

BRIEF DESCRIPTION OF THE DRAWINGS

The present invention will now be further described by way of example with reference to the accompanying the schematic drawings in which:

FIG. 2 shows a competitive assay of the prior art;

FIG. 3 shows a non-competitive assay of the prior art;

FIG. 4 shows an example of an assay according to the present invention;

FIG. 5 shows the response curves obtained by observing the signals emitted by the first developing agent reacting with unoccupied binding agent of the binding sites, and the second developing agent reacting with unoccupied binding sites; and, FIG. 6 shows a comparison of the precision profiles obtained by separate analysis of the competitive and non-competitive data, with the profile obtained when the data are combined by relying on ratio $R_y$, ie the ratio of the signals emitted by both developing agents.

DETAILED DESCRIPTION

Figure 1:
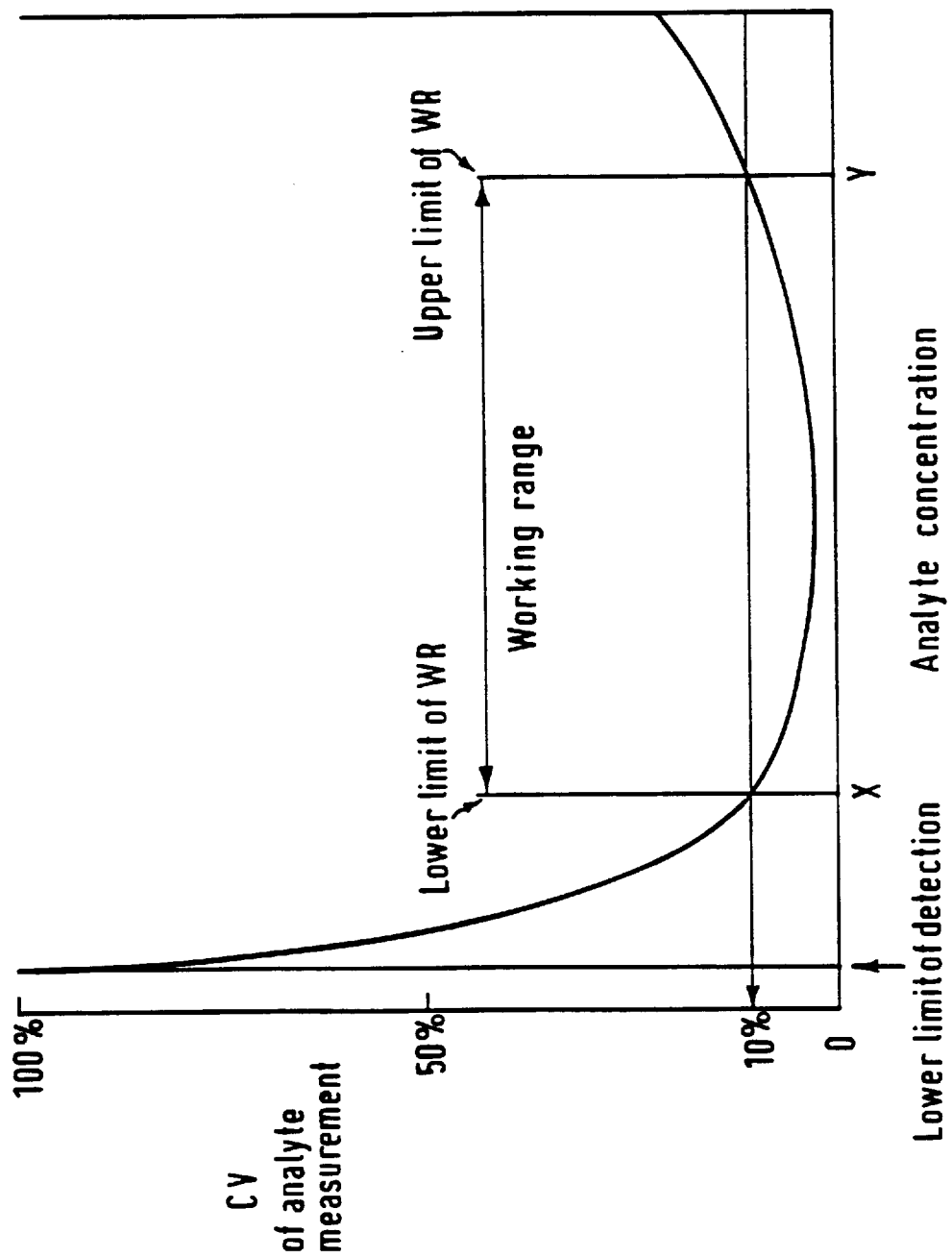
FIG. 1 shows a graph relating error in an assay to its working range, commonly termed the precision profile of the assay.

FIG. 1 illustrates how the precision of an assay varies across its working range. This figure represents the precision profile of an assay, ie the curve relating the error (cv) in the analyte concentration measurement plotted against analyte concentration. The working range of the assay comprises the range of analyte concentrations (between X and Y) within which assay results are of acceptable precision (typically better than 10%). Assay sensitivity is represented by the lower limit of detection, which quantity is typically defined as the analyte concentration below which the cv of the analyte determination exceeds 100%.

However, the cv values used to define the working range and lower limit of detection of an assay are a matter of individual choice, and no generally accepted convention regarding these values exists in the field, notwithstanding widespread acceptance of the general concepts portrayed in FIG. 1.

A sensitive assay is implicitly designed to determine very low analyte concentrations with high precision, ie to yield a very low detection limit. The effective sensitivity of the assay may also be represented by the lower limit of the working range, this value generally correlating closely with the lower limit of detection. Increasing assay sensitivity implies that both the lower limit of detection and the lower limit of the working range (X) are reduced. However, it is common experience that increasing assay sensitivity has the concomitant and undesired effect of also decreasing the upper limit of the working range (Y). In other words, an assay designed for high sensitivity is generally unsuitable for the accurate measurement of high analyte concentrations.

In FIGS. 2 to 4, a binding agent 2 has been immobilised on a support 4. The binding agent has binding sites specific for an analyte 6. After contacting the binding agent 2 with a liquid sample containing the analyte 6, some of the analyte 6 becomes bound to the binding sites of the binding agent 2.

In FIG. 2, a developing agent 8 carrying a marker 10 binds to binding sites on the binding agent 2 unoccupied by analyte 6. The fractional occupancy of the binding sites of the binding agent 2 by the developing agent 8 can be measured by detecting marker 10. This allows the concentration of the analyte 6 in the liquid sample to be ascertained by comparing the signal from the marker 10 against results obtained using a series of standard solutions containing known concentrations of analyte 6.

FIG. 3 shows a non-competitive assay where the analyte 6 bound to the binding sites of the binding agent is detected by back-titrating with a developing agent 12 carrying a marker 14. The binding agent 2 can bind to the bound analyte 6 or to the occupied binding sites of the binding agent. The fractional occupancy of the binding sites by the analyte can then be measured by detecting the marker 14. As with the competitive assay shown in FIG. 2, the signal from the marker 14 can be related to the concentration of the analyte 6 in the liquid sample by reference to the results obtained using a series of solutions of known concentration.

FIG. 4 shows an assay carried out in accordance with the present invention. After the binding agent 2 has been contacted with the analyte 6, a proportion of the binding sites become occupied by analyte 6. The binding agent 2 is then back-titrated using first and second developing agents 8, 12, the developing agents being labelled with first and second markers 10, 14. The markers 10, 14 are chosen to provide distinguishable signals, for instance in the case of fluorescent markers by choosing chromophores which emit light at different frequencies and/or with different fluorescence decay times.

The method of the present invention has some important advantages over the prior art competitive or non-competitive assays.

Firstly, it is found that the use of two developing agents extends the working range over which a given binding assay can be used. This is because at low analyte concentrations, the amount of non-competitive developing agent 12 carrying marker 14 and the detectability of marker 14 are the key determinants of the lower limit of the working range of the binding assay. In other words, very low analyte concentrations are measured with greatest precision by determination of the signals generated by marker 14 carried on developing agent 12, the magnitude of the signals generated marker 10 carried on developing agent 8 being of lesser importance.

Conversely, at high analyte concentrations, it is found that the amount of competitive developing agent carrying marker 10, and the detectability of marker 10, are of greatest importance in determining the upper limit of the working range of the binding assay. In other words, high analyte concentrations are measured with greatest precision by observation of the signals generated by marker 10 carried on developing agent 8, the magnitude of the signals generated by marker 14 carried on developing agent 12 being of lesser importance.

Thus, by measuring the "specific" signals generated by both markers specifically-bound to the binding agent on the solid support, and by minimising the background signals (generated—for example—by developing reagents 8 and 12 non-specifically bound to the solid support) against which the specific signals are determined, the lower limit of the working range can be minimised and the upper limit maximised, thereby extending the working range of the assay system, ie the range of analyte concentrations which can be measured with acceptable precision.

A further advantage arises as the sum of the signals emitted by the two markers when appropriately adjusted to allow for the differing efficiencies with which they are measured, provides a measure of the total amount of binding agent present in the system. In the prior art, knowledge of the total amount of binding agent, or that it is constant, is often a requirement in carrying out assays. As considerable difficulties have been found in past in immobilising on surfaces constant amounts of binding agents (eg antibodies) at even densities, by yielding a measure of both occupied and unoccupied sites, this method allows this problem to be overcome, and the total number of binding sites to be determined.

However, in assays carried out according to the present invention using a small amount of binding agent (eg to bind <5% of the analyte in the sample), it is found that the ratio of the signals from the two markers is solely dependent on the analyte concentration. The basis of this observation is the finding disclosed in International Patent Application WO84/01031 that under such circumstances the fractional occupancy (F) of the binding sites is solely dependent on the ambient analyte concentrations.

Thus, if the total number of binding sites is X, for a given analyte concentration Y, $F_Y X$ sites will be occupied, and $(1-F_Y)$ X sites will be unoccupied. If the measurement efficiency of the signal generated by occupied sites is $\epsilon_1$, and of the signal generated by unoccupied sites is $\epsilon_2$, the ratio $(R_Y)$ of the signals generated from occupied and unoccupied sites is $\epsilon_1 F_Y/\epsilon_2(1-F_Y)$, or $CF_Y/(1-F_Y)$, where $C=\epsilon_1/\epsilon_2=$ constant. Since $F_Y$ is solely dependent on the ambient analyte concentration, and since C is constant for both unknown samples and standards, measurement of $R_Y$ yields a measure of Y irrespective of the exact value of X.

Nevertheless, the use of the ratio $R_Y$ as the response variable is not obligatory, and may indeed be disadvantageous in certain circumstances, eg when the variability in the amount of binding agent situated in the microspot is low, implying that the amount is essentially constant. In these circumstances, it may be preferable to process the competitive and non-competitive assay data separately. The fundamental advantages of combining both competitive and non-competitive assay strategies in accordance with the present invention are not lost thereby.

The method of the present invention also has wider applicability to cases where the amount of binding agent used is large, eg where more than 5% of the total amount of analyte present in the liquid sample is bound. In this case, the ratio of the signals from the two markers is dependent on both the analyte concentration and the amount of binding agent. However, as the amount of binding agent can be determined from sum of the signals from the two markers, a simple correction can be made to obtain the analyte concentration in the sample from the ratio of the two signals.

Thus, the method of the present invention also avoids the necessity of knowing that a constant amount of binding agent is immobilised on different supports, as variations in the amount of binding agent immobilised can readily be corrected for.

Under these circumstances, the sample volume v must either be known or constant.

Let the signal emitted by the label marking the developing agent directed against occupied binding agent binding sites be given by $S_o$;

and the signal emitted by the label marking the developing agent directed against unoccupied binding agent binding sites be given by $S_u$;

and let the constants relating the respective signals to occupied and unoccupied sites be $\epsilon_o$ and $\epsilon_u$ respectively;

and K=the effective equilibrium constant governing the reaction between the analyte and binding agent.

Then, if the analyte concentration in a sample is given by Y;

$$Y=(S_o/\epsilon_o)[\epsilon_u/(KS_u)+1/v]$$

Assuming v is known, this equation contains two unknown constants, $\epsilon_o$ and $\epsilon_u/K$. By determining the signals $S_o$ and $S_u$ for a series of known analyte concentrations, these constants can be determined, and unknown analyte concentrations estimated from corresponding determinations of $S_o$ and $S_u$.

Under ambient analyte conditions, the term 1/v becomes negligible, and $S_o/S_u$ is proportional to the ambient analyte concentration.

EXAMPLE

Reagents
1. Fluorescent hydrophilic latex microspheres, 0.227 μm diameter (Ex 642 nm, Em 653 nm) from Boehringer Mannheim.
2. Sulfate FluoSpheres, 0.1 μm diameter (Ex 490, Em 515 nm) from Molecular Probes.
3. Glycine, Tween20, MES (2-[N-Morpholino] ethanesulfonic acid), di-sodium hydrogen orthophosphate anhydrous, sodium di-hydrogen orthophosphate, ethyl-3 (3-dimethyl amino) propyl carbodimide hydrochloride, RIA grade bovine serum albumin, Trizma and sodium azide from Sigma.
4. Thyroid stimulating hormone (TSH) from NIH USA.
5. Anti-TSH monoclonal capture and developing antibodies from Boehringer Mannheim.

Conjugation of Anti-TSH Mouse Monoclonal Antibody to Fluorescent Hydrophilic Latex Microspheres 1. 10 mg of fluorescent hydrophilic latex microspheres in 0.5 ml double distilled water were added to 0.5 ml of 1% Tween20, shaken for 15 min at room temperature and centrifuged at 8° C. for 10 min at 20,000 rpm in a TSE High-Spin 20 ultracentrifuge.
2. The pellet was dispersed in 2 ml of 0.05M MES (2-[N-Morpholino]ethanesulfonic acid) buffer, pH 6.1 and centrifuged.
3. Step 2 was repeated.
4. The pellet was dispersed in 0.8 ml MES buffer.
5. 2 mg of anti-TSH monoclonal developing antibody in 100 μl were added to the microspheres and shaken for 15 min at room temperature.
6. 100 μl of 0.25% ethyl-3 (3-dimethyl amino) propyl carbodimide hydrochloride were added to the mixture and shaken for 2 hours at room temperature.
7. 10 mg glycine in 100 μl of MES buffer were added to the mixture, shaken for a further 30 min and centrifuged.
8. The pellet was dispersed in 2 ml of 1% BSA, shaken for 1 hour at room temperature and centrifuged.
9. The pellet was dispersed in 2 ml of 1% BSA, shaken for 1 hour at room temperature and centrifuged.
10. The pellet was dispersed in 2 ml of 0.1M phosphate buffer, pH 7.4 and centrifuged.
11. Step 10 was repeated twice.
12. The pellet was dispersed in 2 ml of 1% BSA containing 0.1% sodium azide and stored at 4° C.

Adsorption of TSE to Yellow/Green Sulfate FluoSpheres 1. 50 mg of TSH in 50 μl were added to 4 mg of sulfate FluoSpheres in 350 μl of 0.1M phosphate buffer, pH 7.4 and shaken overnight at room temperature.
2. The preparation was centrifuged at 20,000 rpm, for 15 min at 8° C. in a MSE High-Spin 20 ultracentrifuge.
3. The pellet was dispersed in 2 ml of 1% BSA, shaken for 1 hour and centrifuged.
4. The pellet was dispersed in 2 ml of 0.5% Tween20, shaken for 30 min and centrifuged.
5. The pellet was dispersed in 2 ml of phosphate buffer and centrifuged.
6. Step 4 was repeated twice.
7. The pellet was dispersed in 2ml of 1% BSA containing 0.1% sodium azide and stored at 4° C.

A Combined Competitive and Non-competitive Microspot Sandwich TSE Assay

1. Capture anti-TSH antibody microspots were made by depositing a single 0.5 μl droplet of the antibody at a concentration of 200 μg/ml in 0.1M phosphate buffer, pH 7.4 on each of the black Dynatech MicroFluor microtitre wells. The droplets were aspirated immediately.
2. The wells were flooded with 1% BSA, shaken for 1 hour and washed with phosphate buffer.
3. 200 μl of TSH standards (0, 0.01, 0.03, 0.1, 0.3, 1.0, 3.0, 10, 30, 75, 150 & 300 μU/ml) were added to duplicate wells, these were shaken for 2 hours and washed with phosphate buffer containing 0.05% Tween20.
4. 200μl of 50 μg/ml anti-TSH developing antibody conjugated hydrophilic microspheres for measuring occupied antibody binding sites were added to all wells, these were shaken for 1 hour and washed with phosphate-Tween20 buffer.
5. 200 μl of 50 μg/ml TSH-conjugated sulfate microspheres for measuring unoccupied antibody binding sites were added to all wells, these were shaken for 1 hour, washed with phosphate-Tween20 buffer and scanned with a laser scanning confocal microscope.

FIG. 5 portrays the response curves obtained by observing the signals emitted by the second developing agent (a labelled antibody) reacting with occupied "sensor" antibody binding sites, and the first developing agent (labelled TSH) reacting with unoccupied binding sites. The signals from the first and second markers may be combined to give the ratio $R_Y$, which is plotted against analyte concentration. Thus, FIG. 5 shows that the variation of $R_Y$ with analyte concentration is smooth over a wide range of analyte concentrations, ie the working range of the assay is greater than the prior art competitive or noncompetitive methods.

Figure 6:
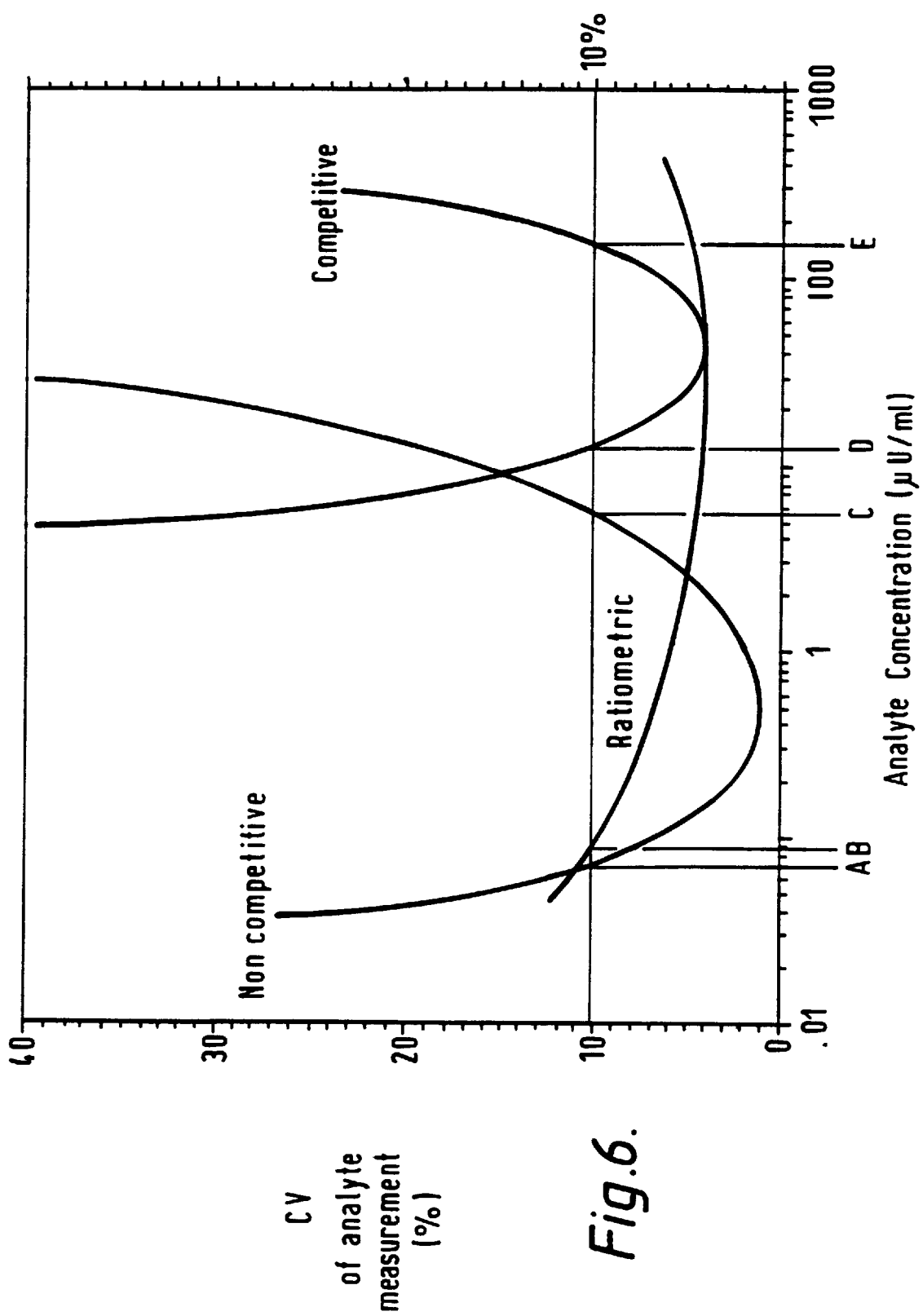

FIG. 6 shows a comparison of the precision profiles obtained by separate statistical analysis of the competitive and non-competitive data, with the profile obtained when the data are combined by relying on the ratio $R_Y$ as the response variable, as discussed above.

Note that the working ranges of both the non-competitive (A to C) and competitive (D to E) assays are considerably more restricted than that of the combined assay which extends from B to above 1000 μU/ml.

This graph also illustrates a phenomenon which may make reliance on the ratio $R_Y$ disadvantageous in certain circumstances. However, in these circumstances it is possible to process the data in a different manner. This phenomenon (the lower precision obtained over certain parts of the range by relying on the ratio as compared with that obtained by processing the data separately) stems from the fact that the statistical error in the ratio may be significantly greater than that in one of the individual measurements, particularly if the amount of binding agent in the microspot is constant. Under the circumstances, samples containing low analyte concentrations may be determined by reliance on the non-competitive data, and high analyte concentrations by reliance on the competitive data.

I claim:
1. A method for determining the concentration of an analyte in a liquid sample comprising:
   (a) contacting the liquid sample with a binding agent having binding sites specific for the analyte so that a fraction of the binding sites become occupied by the analyte;
   (b) back-titrating the binding agent with first and second developing agents, the first developing agent capable of binding to unoccupied binding sites of said binding agent and said first developing agent having a first marker, the second developing agent capable of binding to the bound analyte or to the occupied binding sites and said second developing agent having a second marker different from the first marker;

(c) measuring the signals produced by the first and second markers to provide a value representative of the fraction of the binding sites occupied by the analyte; and, (d) comparing the value to corresponding values obtained from a series of standard solutions containing known concentrations of analyte to obtain the concentration of the analyte in the liquid sample.

2. A method according to claim 1 wherein the liquid sample is contacted with an amount of binding agent which binds less than 5% of the analyte in the sample.

3. A method according to claim 1 wherein the liquid sample is contacted with an amount of binding agent less than 0.1 V/K moles, where V is the volume of the liquid sample and K is the association constant for analyte binding to the binding agent.

4. A method according to claim 1 for determining the concentration of a plurality of different analytes in the liquid sample, using a plurality of binding agents, each binding agent having binding sites specific for a given analyte.

5. A method according to claim 1 wherein the binding agent is immobilised on a support at a discrete location.

6. A method according to claim 5 wherein, in an assay for a plurality of binding agents, the same first and second developing agents are used to back-titrate the plurality of different binding agents, the discrete locations containing the different binding agents being distinguished apart by their location on the support.

7. A method according to claim 1 wherein binding agent having binding sites specific for a particular analyte is immobilised on a support at a plurality of discrete locations so that a series of measurements of the concentration of that analyte are obtained.

8. A method according to claim 5 wherein the binding agent is immobilized at the discrete location as a microspot.

9. A method according to claim 8 wherein the microspot has an area of less than 1 mm$^2$.

10. A method according to claim 6 wherein the discrete location is a microspot.

11. A method according to claim 7 wherein the discrete location is a microspot.

12. A method according to claim 5 wherein the microspot has an area of less than 1 mm$^2$.

13. A method according to claim 6 wherein the microspot has an area of less than 1 mm$^2$.

14. A method according to claim 7 wherein the microspot has an area of less than 1 mm$^2$.

15. A kit for determining the concentration of an analyte in a liquid sample according to the method of claim 1, the kit comprising:

(a) a solid substrate having attached thereto binding agent, the binding agent having binding sites specific for the analyte, (b) back-titration reagents comprising first and second developing agents, the first developing agent capable of binding to unoccupied binding sites of said binding agent and said first developing agent having a first marker, the second developing agent capable of binding to the bound analyte or to occupied binding sites and said second developing agent having a second marker different from the first marker.

16. A method according to claim 1 wherein the binding agent is an antibody having binding sites specific for an analyte which is an antigen.

17. A method according to claim 1 wherein the binding agent is an oligonucleotide having binding sites specific for a nucleic acid analyte.

18. A method according to claim 2 wherein the binding agent is an antibody having binding sites specific for an analyte which is an antigen.

19. A method according to claim 2 wherein the binding agent is an oligonucleotide having binding sites specific for a nucleic acid analyte.

20. A method according to claim 3 wherein the binding agent is an antibody having binding sites specific for an analyte which is an antigen.

21. A method according to claim 3 wherein the binding agent is an oligonucleotide having binding sites specific for a nucleic acid analyte.

22. A method according to claim 4 wherein the binding agent is an antibody having binding sites specific for an analyte which is an antigen.

23. A method according to claim 4 wherein the binding agent is an oligonucleotide having binding sites specific for a nucleic acid analyte.

24. A method according to claim 5 wherein the binding agent is an antibody having binding sites specific for an analyte which is an antigen.

25. A method according to claim 5 wherein the binding agent is an oligonucleotide having binding sites specific for a nucleic acid analyte.

26. A method for determining a value which is representative of a fraction of binding sites of a binding agent that are occupied by analyte present in a liquid sample, said binding sites being specific for said analyte, said method comprising:

(a) contacting the liquid sample with the binding agent so that a fraction of the binding sites become occupied by the analyte;

(b) back-titrating the binding agent with first and second developing agents, the first developing agent capable of binding to unoccupied binding sites of said binding agent and said first developing agent having a first marker, the second developing agent capable of binding to the bound analyte or to the occupied binding sites and said second developing agent having a second marker different from the first marker; and (c) measuring the signals produced by the first and second markers to provide a value representative of the fraction of the binding sites occupied by the analyte.

27. A method according to claim 26, wherein at least one binding agent is immobilized on a solid support at at least one discrete location.

28. A method of claim 1 further comprising the following steps:

(d) comparing the value representative of the fraction of the binding sites occupied by the analyte to corresponding values obtained from a series of standard solutions containing known concentrations of analyte to obtain the concentration of the analyte in the liquid sample.

29. A method according to claim 1 wherein the liquid sample is contacted with an amount of binding agent which binds less than 5% of the analyte in the sample.

30. A method according to claim 29 wherein the liquid sample is contacted with an amount of binding agent that is less than 0.1 V/K moles, where V is the volume of the liquid sample and K is the association constant for analyte binding to the binding agent.

31. A method according to claim 30 wherein the binding agent is immobilized at the discrete location as a microspot.

* * * * *